(12) United States Patent
Dave et al.

(10) Patent No.: US 8,889,183 B2
(45) Date of Patent: Nov. 18, 2014

(54) BIOCIDE COMPOSITION

(75) Inventors: Parthiv Ripudaman Dave, Mumbai (IN); Girish Umakant Jambekar, Mumbai (IN)

(73) Assignee: Conopco, Inc., Englwood Cliffs, NJ (US)

( * ) Notice: Subject to any disclaimer, the term of this patent is extended or adjusted under 35 U.S.C. 154(b) by 14 days.

(21) Appl. No.: 13/818,176

(22) PCT Filed: Aug. 12, 2011

(86) PCT No.: PCT/EP2011/063914
§ 371 (c)(1),
(2), (4) Date: Feb. 21, 2013

(87) PCT Pub. No.: WO2012/028437
PCT Pub. Date: Mar. 8, 2012

(65) Prior Publication Data
US 2013/0156838 A1    Jun. 20, 2013

(30) Foreign Application Priority Data

Aug. 31, 2010 (IN) .......................... 2417/MUM/2010
Oct. 22, 2010 (EP) ...................................... 10188447

(51) Int. Cl.
*A01N 43/50*  (2006.01)
*A01N 43/66*  (2006.01)
*A01N 59/14*  (2006.01)
*A01N 59/00*  (2006.01)
*A01N 25/08*  (2006.01)

(52) U.S. Cl.
CPC ................ *A01N 59/14* (2013.01); *A01N 43/50* (2013.01); *A01N 59/00* (2013.01)

USPC ........... 424/465; 504/151; 504/153; 504/155; 504/156

(58) Field of Classification Search
USPC ........... 504/151, 152, 155, 156, 153; 424/465
See application file for complete search history.

(56) References Cited

U.S. PATENT DOCUMENTS

2008/0107701 A1    5/2008    Rawat et al.

FOREIGN PATENT DOCUMENTS

WO    WO2006006155 A2    1/2006

OTHER PUBLICATIONS

EP Search Report EP 10 18 8447 dated Apr. 19, 2011.
PCT Internatiional Search Report PCT/EP2011/063914 dated Jan. 30, 2012.
PCT Written Opinion PCT/EP2011/063914 dated Jan. 30, 2012.

*Primary Examiner* — John Pak
(74) *Attorney, Agent, or Firm* — Greenberg Traurig, LLP

(57) ABSTRACT

The present invention relates to a novel biocide composition for use in gravity fed water purification devices and suitable for purifying water for drinking purposes and a process for preparing the novel biocide composition. The biocide tablet composition comprises one or more halogenated 5,5-dialkylhydantoin compound; a chlorine biocide compound selected from trichloroisocyanuric acid (TCCA) or sodium dichloroisocyanurate (NaDCC) or mixtures thereof; 0.1-1.0% water soluble boron containing compound; wherein the ratio between the halogenated 5,5-dialkylhydantoin compound and chlorine biocide compound is in the range 85:15 to 65:35 and the average particle size of the halogenated 5,5-dialkylhydantoin compound and chlorine biocide compound is in the range 400 to 1200 microns.

13 Claims, No Drawings

BIOCIDE COMPOSITION

FIELD OF INVENTION

The present invention relates to a novel biocide composition for use in gravity fed water purification devices and suitable for purifying water for drinking purposes and a process for preparing the novel biocide composition.

Any discussion of the prior art throughout the specification should in no way be considered as an admission that such prior art is widely known or forms part of the common general knowledge in the field.

BACKGROUND AND PRIOR ART

Many people in the world live in countries where there is a severe shortage of hygienic potable water. People in these areas have to depend directly on ground water sources like wells, ponds and rivers. Often these water sources are contaminated by sewage, industrial effluents and agricultural byproducts. These areas are generally small villages that do not have municipal drinking water treatment plants. Hence these people have to treat the water themselves before consuming it. The water from these sources is often collected by the people in buckets or pots in small quantities like ten to twenty liters for potable consumption for a day's use. The most common method to produce clean water is boiling. However many people cannot afford to boil the water since it requires fuel like coal, or wood which are expensive and scarcely available.

These people often cannot depend on other methods of water purification like use of UV treatment devices or membrane filtration devices. This is because these devices require availability of electric power which is often not available on a continuous basis in these areas.

Some gravity fed water filters for domestic use have been described in the past. These purifiers use a suitable biocide to make the water microbiologically safe for drinking. The most commonly used biocides are halogen containing compounds. One group of commonly used halogen releasing compounds is trichloroisocyanuric acid (TCCA) and sodium dichloroisocyanurate (NaDCC). Another class of halogen releasing biocides are hydantoins and the most commonly used compound is 1-bromo-3-chloro-5,5-dimethylhydantoin (BCDMH).

WO2006/006155 (Bromine Compounds Ltd.), discloses a method of making a physically strong, solid tablet having a mixture of halogenated 5,5-dimethylhydantoin and chlorine biocide compound. Specific ratios of BCDMH and TCCA are also disclosed. The disclosure is mainly for water treatment like industrial water, waste water, pulp & paper industry process water, cooling towers, swimming pools, spas and institutional and domestic applications and the like and hence the tablet size is large and is about 10-300 g in weight.

In a gravity fed water purification device, unlike the proposed use suggested in the prior art which is for a pool of water such as a swimming pool or a spa or a cooling tower, the biocide tablet is eroded as the water to be purified passes over it in a controlled fashion thereby ensuring a reasonable constant contact surface area between water and biocide tablet so that the amount of biocide released into the water is more or less at a uniform concentration. The tablet is in contact with water for a period where about 1000-2000 liters of water are passed over it over 3-8 months. A biocide tablet that is used in a gravity fed water purification device is generally small sized and weighing about 2-8 g. It is necessary that in such a situation the tablets do not chip off or break off and if it does the concentration in that pool of water would be very high which is undesirable. Thus it is essential to ensure a reasonable constant contact surface area between water and biocide tablet, and thus maintaining the tablet integrity becomes very important.

The present inventors have found that use of a combination of a halogenated 5,5-dialkyllhydantoin and a chlorine biocide compound such as TCCA and NaDCC, provide superior benefits in purifying water and making it microbiologically safe. However, manufacturing tablets of smaller size using the combination of a halogenated 5,5-dialkyllhydantoin and chlorine biocide compound is a problem as the tablet strength gets affected and the tablets are very brittle and thus break very easily.

The present inventors have found that by selecting a specific range of particle size of the materials and using a water soluble boron containing compound at selected range it is possible to obtain tablets weighing 2-8 g with good tablet strength, comprising a mixture of a halogenated 5,5-dialkyllhydantoin and a chlorine biocide compound. These tablets maintain the integrity of the tablets even when they are in continuous contact in water and they also have uniform erosion properties even when they are immersed in a stream of water for a prolonged period of time by maintaining a constant contact surface area between water and biocide tablet.

It is thus the basic object of the present invention to provide a biocide tablet comprising one or more halogenated 5,5-dialkyllhydantoins and chlorine biocide compounds, weighing 2-8 g with good tablet strength.

Another object of the present invention is directed to provide a biocide tablet comprising one or more halogenated 5,5-dialkyllhydantoins and chlorine biocide compounds, weighing 2-8 g with good tablet strength, having uniform erosion properties even when they are immersed in a stream water for a prolonged period of time.

Yet another object of the present invention is to provide a uniform concentration of the biocide in water by maintaining good integrity and erosion properties of the tablets in a water purification device.

SUMMARY OF THE INVENTION

According to the present invention there is provided a biocide tablet composition comprising:
  a) one or more halogenated 5,5-dialkylhydantoin compounds;
  b) a chlorine biocide compound selected from trichloroisocyanuric acid (TCCA), sodium dichloroisocyanurate (NaDCC), and mixtures thereof;
  c) 0.1 to 1.0% of a water soluble boron containing compound;
wherein the ratio between the halogenated 5,5-dialkylhydantoin compound and chlorine biocide compound is in the range 85:15 to 65:35 and the average particle size of the halogenated 5,5-dialkylhydantoin compound and chlorine biocide compound is in the range 400 to 1200 microns.

According to another aspect of the present invention there is provided a process of preparing a biocide tablet comprising
  a) one or more halogenated 5,5-dialkylhydantoin compounds,
  b) a chlorine biocide compound selected from trichloroisocyanuric acid (TCCA), sodium dichloroisocyanurate (NaDCC), and mixtures thereof, and
  c) 0.1 to 1.0% water soluble boron containing compound,
said process comprising:
  i. mixing the halogenated 5,5-dialkylhydantoin compound and the chlorine biocide compound in a ratio 85:15 to 65:35 wherein the average particle size of the halogenated 5,5-dialkylhydantoin compound and chlorine biocide compound is in the range of 400 to 1200 microns in the presence of the boron containing compound;

ii. compressing the mixed mass using a force adjusted between 2 and 7 tonnes to produce the tablet of the desired strength.

DETAILED DESCRIPTION OF THE INVENTION

For the avoidance of doubt, any feature of one aspect of the present invention may be utilised in any other aspect of the invention. It is noted that the examples given in the description below are intended to clarify the invention and are not intended to limit the invention to those examples per se.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Unless specified otherwise, numerical ranges expressed in the format "from x to y" are understood to include x and y. When for a specific feature multiple preferred ranges are described in the format "from x to y", it is understood that all ranges combining the different endpoints are also contemplated.

According to the present invention there is provided a biocide tablet composition comprising:
a) one or more halogenated 5,5-dialkylhydantoin compounds;
b) a chlorine biocide compound selected from trichloroisocyanuric acid (TCCA), sodium dichloroisocyanurate (NaDCC), and mixtures thereof;
c) 0.1 to 1.0% of a water soluble boron containing compound;
wherein the ratio between the halogenated 5,5-dialkylhydantoin compound and chlorine biocide compound is in the range 85:15 to 65:35 and the average particle size of the halogenated 5,5-dialkylhydantoin compound and chlorine biocide compound is in the range 400 to 1200 microns.

The halogenated 5,5-dialkylhydantoin compound may be selected from 1-bromo-3-chloro-5,5-dimethylhydantoin, 1-chloro-3-bromo-5,5-dimethylhydantoin, 1,3-dibromo-5,5-dimethylhydantoin (DBDMH) or mixtures of 1-bromo-3-chloro-5,5-dimethylhydantoin and 1-chloro-3-bromo-5,5-dimethylhydantoin and 1,3-dibromo-5,5-dimethylhydantoin and 1,3-dichloro-5,5-dimethylhydantoin or any combination thereof.

The most preferred halogenated 5,5-dialkylhydantoin compound is 1-bromo-3-chloro-5,5-dimethylhydantoin (BCDMH).

Although the chlorine biocide compound may be selected from trichloroisocyanuric acid (TCCA), sodium dichloroisocyanurate (NaDCC), and mixtures thereof, the most preferred chlorine biocide is trichloroisocyanuric acid (TCCA).

The water soluble boron compound may be selected from Alkali borate, borax, Alkali hydrogen borate and the most preferred water soluble boron compound is boric acid. The level of the water soluble boron compound in the biocide composition is in the range from 0.1 to 1.0% and more preferably from 0.1 to 0.5%.

The preferred ratio between the halogenated 5,5-dialkylhydantoin compound and chlorine biocide compound is preferably in the range 80:20 to 70:30 and the most preferred ratio is 70:30.

The average particle size of the halogenated 5,5-dialkylhydantoin compound and chlorine biocide compound is in the range 400 to 1200 microns. The preferred average particle size range is 800 to 1000 microns.

The particle size of the water soluble boron containing compound is 50-100 microns and preferably 60-75 microns.

Tablet dimensions are preferably 16.4+/−0.3 mm diameter and 6 mm to 22 mm height and more preferably 16.4+/−0.3 mm diameter and height 10 mm to 21 mm.

The tablet is preferably obtainable by the process below.

According to another aspect of the present invention there is provided a process of preparing a biocide tablet comprising
a) one or more halogenated 5,5-dialkylhydantoin compounds,
b) a chlorine biocide compound selected from trichloroisocyanuric acid (TCCA), sodium dichloroisocyanurate (NaDCC), and mixtures thereof, and
c) 0.1 to 1.0% water soluble boron containing compound,
said process comprising:
i. mixing the halogenated 5,5-dialkylhydantoin compound and the chlorine biocide compound in a ratio 85:15 to 65:35 wherein the average particle size of the halogenated 5,5-dialkylhydantoin compound and chlorine biocide compound is in the range of 400 to 1200 microns in the presence of the boron containing compound;
ii. compressing the mixed mass using a force adjusted between 2 and 7 tonnes to produce the tablet of the desired strength.

The temperature during the process is preferably in the range 15-30° C. and more preferably is in the range 20-25° C. The ambient Relative humidity is maintained between 40-65% during the processing and more preferably is between 50-55%.

It is preferred that the 5,5-dialkylhydantoin is first fed into the mixer followed by the addition of the chlorine biocide under continuous mixing. Then the water soluble boron containing compound is added and mixing is continued preferably for 10-20 minutes. The mixer used is preferably a ribbon mixer. The mixed mass is used for the tablet making.

It is preferred that a 15 Ts rotary tablet machine is used for tablet making. The force is adjusted between 2-7 Ts and preferably between 3-5 Ts to produce the tablet of the desired strength.

Preferably, the one or more halogenated 5,5-dialkylhydantoin compounds are one or more 5,5-dimethylhydantoin compounds.

Preferably, the water soluble boron containing compound is a water soluble borate compound.

Preferably, the average particle size of the halogenated 5,5-dialkylhydantoin compound and chlorine biocide compound is 800 to 1000 microns.

According to another aspect the present invention provides a biocide tablet composition comprising:
a) one or more halogenated 5,5-dialkylhydantoin compounds;
b) a chlorine biocide compound selected from trichloroisocyanuric acid (TCCA), sodium dichloroisocyanurate (NaDCC), and mixtures thereof; and
c) 0.1-1.0% of a water soluble boron containing compound;
wherein the ratio between the halogenated 5,5-dialkylhydantoin compound and chlorine biocide compound is in the range 85:15 to 65:35 and the tablet is obtainable by the process according to the invention.

The details of the invention its objects and advantages are explained hereunder in greater detail in relation to non-limiting examples:

EXAMPLES

Example 1 i. Process for Preparing the Tablets

A batch of 20 kgs was prepared. 14.0 kgs of 1-bromo-3-chloro-5,5-dimethyllhydantoin (BCDMH), obtained from Lonza Ltd, Switzerland, was taken in a Ribbon mixer and to this 5.9 kgs of Trichloro cyanuric acid (TCCA), obtained from Occidental Chemical Corporation, USA was added under continuous mixing. The average particle size of BCDMH and TCCA used was 800 microns. This was followed by the addition of 0.1 kg of Boric acid with a particle size of 75 microns, obtained from Indo Borax and Chemicals Ltd, India, and the mixing was continued for 10 minutes. The mixed mass was used for the tablet making using a 15 Ts rotary tablet machine under a force adjusted to 4 Ts to produce the tablet of the desired strength. During the processing the temperature was maintained at 20+/−2° C. and relative humidity between 50-55%. Maintaining such processing conditions delivers the most uniform and stable tablets. The above mentioned quantities would obtain tablets with the ratio of BCDMH:TCCA:Boric acid as 70:29.5:0.5. For making comparisons with other ratios the quantities of BCDMH, TCCA and Boric acid were varied suitably and presented in Table 1.

ii. Measurement of Tablet Strength

The breaking strength of the tablet was measured by using a table top tablet crushing instrument which was calibrated to measure up to 25 kg/cm$^2$ compaction pressure. The tablet was mounted onto the device and the compaction was increased from zero gradually till the tablet breaks. The pressure at which the tablet breaks was noted down from the calibrated scale. The data for various ratios of BCDMH, TCCA and Boric acid is presented in Table 1.

TABLE 1

| Formulation | BCDMH & TCCA Proportion | Boric acid | Breaking strength (kgs/cm$^2$) |
|---|---|---|---|
| 1 | 100:0 | 0.1 | 6.0 (Tablet breaks, poor strength) |
| 2 | 100:0 | 0.0 | 6 (capping at the edge, tablet breaks) |
| 3 | 90:10 | 0.1 | 7.5 (Tablet breaks, poor strength) |
| 4 | 90:10 | 0.0 | 7 (capping at the edge, tablet breaks) |
| 5 | 80:20 | 0.1 | 9.0 (Tablet chips at the edge, acceptable strength) |
| 6 | 80:19.5 | 0.5 | 11.0 (Good tablet strength) |
| 7 | 80:20 | 0.0 | 8 (capping at the edge) |
| 8 | 70:30 | 0.1 | 12.0 (Good tablet strength) |
| 9 | 70:29.5 | 0.5 | 16.0 (Excellent tablet strength) |
| 10 | 70:29.25 | 0.75 | 13.0 (Very good tablet strength) |
| 11 | 70:30 | 0.0 | 10.5 (Slight capping at the edge moderate tablet strength) |

The data presented in Table 1 show that when the ratios and the average particle size of BCDMH, TCCA were within the claimed range according to the invention and the tablet composition had the required level of boric acid, tablets with good strength were formed. In the absence of boric acid even if the selected particle size was used the tablet strength was poor.

iii. Effect of Particle Size on Tablet Strength and Tablet Erosion

The tablets with BCDMH: TCCA at 70:30 were prepared using materials with various average particle sizes as shown in Table 2 and tablet strength was measured as per Example 1. The data on tablet erosion was measured by using the biocide tablets with a composition and particle size as mentioned in Table 1, in a regular gravity fed water purifier comprising a filtration unit adapted to separate particulate and soluble material from the input water, which is in fluid communication with a chemical dispensing unit such that flow rate of water exiting the filtration unit is controlled by a flow control means before the water encounters a biocide dispensed by the chemical dispensing unit, the water thereafter being retained in a retention chamber for a predetermined period of time before exiting the water purification system through a scavenger means adapted to separate the dispensed biocide from the exit water. 1500 liters of water was passed in the device and the tablet strength and erosion parameters were measured and the data are presented in Table 2. Comparison of the effect of particle size with and without the addition of boric acid was also made.

TABLE 2

| Composition | Average Particle size in microns of BCDMH and TCCA | Breaking strength (kgs/cm$^2$) | Biocide Concentration in water |
|---|---|---|---|
| 12 | 800 BCDMH:TCCA::70:30 without Boric acid | 11 (Fairly good tablet strength, fairly uniform erosion of tablet) | Fairly uniform erosion of tablet but beyond the required range. |
| 13 | 800 but BCDMH:TCCA:Boric acid at 70:29.5:0.5 | 16.0 (Excellent tablet strength) | 3 ppm +/− 0.1 |
| 14 | 800 but BCDMH:TCCA:Boric acid at 70:29.25:0.75 | 13.0 (Very good tablet strength) | 3 ppm +/− 0.1 |
| 15 | 1400 BCDMH:TCCA::70:30 without Boric acid | 5 (capping at the edge, uneven erosion of tablet) | Highly varied, may be very low or very high. |
| 16 | 200 BCDMH:TCCA::70:30 without Boric acid | 7 (capping at the edge, uneven erosion of tablet) | Highly varied, may be very low or very high. |
| 17 | 1400 BCDMH:TCCA:Boric acid at 70:29.5:0.5 | 7 (capping at the edge, uneven erosion of tablet) | Highly varied, may be very low or very high. |
| 18 | 200 BCDMH:TCCA:Boric acid at 70:29.5:0.5 | 9 (capping at the edge, uneven erosion of tablet) | Highly varied, may be very low or very high. |

The data presented in Table 2 show that when the average particle size was within the range of the invention the tablet strength was good with fairly uniform erosion properties. However, if the average particle size was above or below the required value the tablet show capping and the erosion properties were uneven. In order to obtain very good tablet strength and leaching of the biocide to be uniform with a concentration in the range 3 ppm+/−0.1, addition of boric acid was essential apart from maintaining the required particle size. When the particle size used for making the biocide tablet was beyond the required size then the leaching of the biocide was very varied. It was very high depending on chipping of the tablet or was be very low.

The invention claimed is:

1. A biocide tablet composition comprising:
   a) one or more halogenated 5,5-dialkylhydantoin compounds;
   b) a chlorine biocide compound selected from the group consisting of trichloroisocyanuric acid (TCCA), sodium dichloroisocyanurate (NaDCC), and mixtures thereof; and
   c) 0.1-1.0% of a water soluble boron containing compound; wherein a ratio between the halogenated 5,5-dialkylhydantoin compound and the chlorine biocide compound is in a range of 85:15 to 65:35; and
   wherein the biocide tablet composition has a breaking strength of 11 kgs/cm$^2$ to 16 kgs/cm$^2$.

2. A biocide tablet composition as claimed in claim 1 wherein the 5,5-dialkylhydantoin compound is 1-bromo-3-chloro-5,5-dimethylhydantoin (BCDMH).

3. A biocide tablet composition as claimed in claim 1 wherein the chlorine biocide compound is trichloroisocyanuric acid (TCCA).

4. A biocide tablet composition as claimed in claim 1 wherein the water soluble boron containing compound is boric acid.

5. A biocide tablet composition as claimed in claim 1 wherein a ratio between the halogenated 5,5-dialkylhydantoin compound and the chlorine biocide compound is 70:30.

6. A biocide tablet composition as claimed in claim 1 wherein a weight of the tablet is 2 g to 8 g.

7. A process of preparing a biocide tablet comprising: mixing, in the presence of 0.1 to 1.0% of a water soluble boron containing compound, one or more halogenated 5,5-dialkylhydantoin compounds and a chlorine biocide compound selected from the group consisting of trichloroisocyanuric acid (TCCA), sodium dichloroisocyanurate (NaDCC), and mixtures thereof in a ratio 85:15 to 65:35;
   wherein an average particle size of the halogenated 5,5-dialkylhydantoin compounds and an average particle size of the chlorine biocide compound is 400 to 1200 microns and
   compressing the mix mass using a force adjusted between 2 and 7 tonnes to produce the tablet, wherein the tablet comprises the one or more halogenated 5,5-dialkylhydantoin compounds and the chlorine biocide compound.

8. A process of preparing a biocide tablet as claimed in claim 7 wherein a temperature during the process is in the range from 15 to 30° C.

9. A process of preparing a biocide tablet as claimed in claim 7 wherein a temperature during the process is in the range from 20 to 25° C.

10. A process of preparing a biocide tablet as claimed in claim 7, wherein the one or more halogenated 5,5-dialkylhydantoin compounds are one or more 5,5-dimethylhydantoin compounds.

11. A process of preparing a biocide tablet as claimed in claim 7, wherein the water soluble boron containing compound is a water soluble borate compound.

12. A process of preparing a biocide tablet as claimed in claim 7 wherein the average particle size of the halogenated 5,5-dialkylhydantoin compound and the average particle size of the chlorine biocide compound is 800 to 1000 microns.

13. A process of preparing a biocide tablet as claimed in claim 7 wherein the tablet has a breaking strength of 11 kgs/cm$^2$ to 16 kgs/cm$^2$.

* * * * *